United States Patent [19]

Carmosin

[11] 4,125,537
[45] Nov. 14, 1978

[54] PREPARATION OF PYRROLE-2-ACETATES

[75] Inventor: Richard J. Carmosin, Philadelphia, Pa.

[73] Assignee: McNeil Laboratories, Incorporated, Ft. Washington, Pa.

[21] Appl. No.: 766,305

[22] Filed: Feb. 7, 1977

[51] Int. Cl.$^2$ ............................................. C07D 207/32
[52] U.S. Cl. .................................. 260/326.2; 424/274
[58] Field of Search ...................................... 260/326.2

[56] References Cited

U.S. PATENT DOCUMENTS

| | | | |
|---|---|---|---|
| 3,544,589 | 12/1970 | Orth et al. ........................ | 260/326.2 |
| 3,752,826 | 8/1973 | Carson ........................... | 260/326.5 J |
| 3,803,169 | 4/1974 | Carson ........................... | 260/326.5 J |
| 3,846,447 | 11/1974 | Carson ........................... | 260/326.5 J |
| 3,957,818 | 5/1976 | Carson ........................... | 260/326.46 |

OTHER PUBLICATIONS

J. Prakt. Chem. vol. 35, p. 41 (1967).

Primary Examiner—Donald G. Daus
Assistant Examiner—Mary C. Vaughn
Attorney, Agent, or Firm—Salvatore R. Conte

[57] ABSTRACT

Loweralkyl 1-loweralkyl-pyrrole-2-glyoxylates are reduced by the base-catalyzed action of hydrogen sulfide under pressure of at least 30 p.s.i. to loweralkyl 1-loweralkyl-pyrrole-2-acetates.

4 Claims, No Drawings

PREPARATION OF PYRROLE-2-ACETATES

BACKGROUND OF THE INVENTION

In J. Prakt. Chem., 35, 41 (1967), the base-catalyzed action of hydrogen sulfide on certain 1, 2-diketones and certain glyoxylic acid esters are reported. However, the reduction of pyrroleglyoxylic acid esters and the marked improvement in the process occassioned by utilizing pressure, which characterizes this invention, are not disclosed in this reference. The end products of the process of the subject invention are 1-loweralkyl-pyrrole-2-acetates (I) which have been reported in the literature as being useful intermediates in the preparation of 5-aroyl-pyrrole-2-acetic acid derivatives having antiinflammatory activity (e.g., see U.S. Pat. Nos. 3,752,826; 3,803,169; 3,846,447 and 3,957,818).

DESCRIPTION OF THE PREFERRED EMBODIMENTS

This invention relates to an improved process of preparing loweralkyl 1-loweralkyl-pyrrole-2-acetates of the formula:

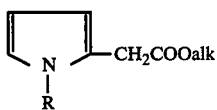

(I)

wherein R is loweralkyl, preferably methyl; and alk is loweralkyl.

As used herein, "loweralkyl" refers to straight or branch chained alkyls having from 1 to 6 carbons, for example, methyl, ethyl, propyl, isopropyl, butyl, tert-butyl, pentyl, hexyl and the like.

According to the instant process, an appropriate loweralkyl 1-lowerakyl-pyrrole-2-glyoxylate of formula (II) wherein R and alk are as previously defined, is reduced to the corresponding loweralkyl 1-loweralkyl-pyrrole-2-acetate of formula (I) by the base-catalyzed action of hydrogen sulfide under pressure:

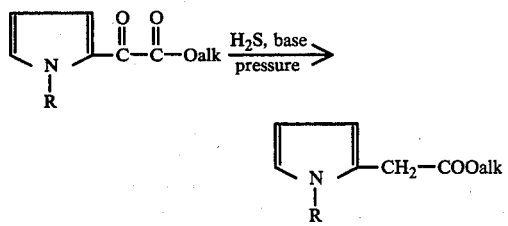

Base catalysts suitable for the foregoing reduction reaction are tertiary amines, for example, a tertiary alkyl amine, such as, triethylamine, diisopropylethylamine and the like; a heterocyclic amine, e.g., triethylenediamine, N-methylpyrrolidine, N-methyl-piperidine, N-methyl-piperazine and the like; and a heteroaryl amine, e.g., pyridine, 2-hydroxy-pyridine, imidazole, N-methyl-imidazole, bipyridyl and the like. The most preferred amines are pyridine, imidazole and N-methyl-piperidine.

Base catalysts which are liquids and also suitable as solvents for the reduction reaction, e.g., pyridine, triethylamine and the like, may be employed without the use of additional solvent. Other solvents that may be utilized for the reduction reaction, although less preferred, are dipolar aprotic organic solvents, such as, for example, N,N-dimethylformamide (DMF), dimethyl sulfoxide (DMSO), hexamethylphosphoramide (HMPA) and the like.

The reaction temperature is not critical and temperatures varying from ambient temperature to about 120° C. may be conveniently utilized, although elevated temperatures are advantageously employed to enhance the rate of reaction and temperatures varying from about 60° C. to about 100° C. are preferred.

The reduction reaction is run in an appropriate sealed vessel capable of withstanding an internal pressure of at least 30 p.s.i. of gaseous hydrogen sulfide. The preferred pressure range is from about 50 to about 500 p.s.i. although pressures up to about 1000 p.s.i. may be employed.

In accordance with this invention, there is provided an improved process of reducing a loweralkyl 1-loweralkyl-pyrrole-2-glyoxylate to a loweralkyl 1-loweralkyl-pyrrole-2-acetate by the amine-catalyzed action of hydrogen sulfide in a tertiary amine solvent or a dipolar aprotic organic solvent, the improvement comprising the reduction being conducted under a pressure of at least 30 p.s.i. Accordingly, a marked increase in percent conversion from glyoxylate precursor to acetate product is obtained.

The following examples are provided for purposes of illustrating the subject invention but not for limiting same thereto.

EXAMPLE I

A solution of 50g of methyl 1-methylpyrrole-2-glyoxylate in 200 ml of pyridine is cooled to −78° C. and 64g of hydrogen sulfide is added. The mixture is sealed in a stirred autoclave and heated to 63° C. The pressure rises to about 130 p.s.i. After 27 hrs., the hydrogen sulfide is driven off in a nitrogen stream and the solution is decanted from the precipitated sulfur. Pyridine is distilled off at 20 mm Hg. The residue is distilled at 0.03 mm Hg, b.p. 68–70° C., to give 39.2g of oily methyl 1-methylpyrrole-2-acetate (86% yield).

EXAMPLE II

A solution of 25g of methyl 1-methyl 1-methylpyrrole-2glyoxylate, 23g of hydrogen sulfide and 100 ml of pyridine is sealed in an autoclave and stirred 46 hrs. at 25° C. under pressure of 60 p.s.i. The pressure is released and the solution decanted from precipitated sulfur. The solution is taken up in ether and washed successively with potassium carbonate solution, dilute hydrochloric acid, sodium bicarbonate solution and brine. The solution is then dried over $MgSO_4$ and the solvent evaporated in vacuo. The residual oil is distilled at 0.001 to 0.005 mm Hg to give 18.8g of oily methyl 1-methylpyrrole-2-acetate (82% yield).

EXAMPLE III

A solution of 44g (0.26 mole) of methyl N-methyl-2-pyrrole-2-glyoxylate in 110g (1.4 mole) of pyridine is placed in a stirred autoclave. The solution is pressurized with hydrogen sulfide gas, with stirring, until the pressure is stabilized at about 200 p.s.i. Stirring is continued at room temperature for four hours. The pressurized vessel is opened and the contents assayed by gas liquid chromatography (GLC) indicating 33% of the product, methyl-1-methylpyrrole-2-acetate.

EXAMPLE IV

A mixture of 1g of the loweralkyl 1-methylpyrrole-2-glyoxylate and quantities of the solvent and catalyst, shown in Table I, hereafter are cooled to −60° C. and 1.8g hydrogen sulfide is added. Each of mixtures is sealed in a pressure bottle and warmed to the indicated temperature. After the specified reaction time, the mixture is diluted with chloroform and analyzed by gas liquid chromatography against triphenylmethane internal standard (OV 17; 90°–280° C.) to yield the indicated percent conversion for each of the respective loweralkyl 1-methylpyrrole-2-acetates obtained as corresponding products.

TABLE 1

| Alkyl | Catalyst | Solvent | Time (hrs.) | Temp. (° C.) | % Conversion |
|---|---|---|---|---|---|
| $CH_3$ | pyridine, 2.6 ml | (pyridine) | 4 | 25 | 27 |
| $CH_3$ | imidazole, .224g | pyridine, 2.6 ml | 4 | 25 | 39 |
| $CH_3$ | N-methylimidazole; .27g | DMSO, 10.6 ml | 4 | 25 | 16 |
| $CH_3$ | imidazole, 2.24g | DMSO, 10.6 ml | 4 | 25 | 29 |
| $CH_3$ | 2-hydroxypyridine, 1.1g | pyridine, 4 ml | 4 | 25 | 33 |
| $C_2H_5$ | triethylenediamine, 0.34g | DMSO, 10.6 ml | 4 | 25 | 17 |
| $C_2H_5$ | 2,2-bipyridyl, 4.75g | DMSO, 20.6 ml | 4 | 25 | 6.9 |
| $C_2H_5$ | pyridine, 2.6 ml | DMSO, 10.6 ml | 4 | 25 | 15.6 |
| $C_2H_5$ | pyridine, 2.6 ml | (pyridine) | 4 | 25 | 23 |
| $C_2H_5$ | triethylamine, 4.2 ml | (triethylamine) | 4 | 25 | 7.5 |
| $C_2H_5$ | imidazole, 0.9g | pyridine, 4 ml | 4 | 77 | 91 |
| $CH_3$ | N-methylpyrrolidine, 3.4 ml | (N-Me-pyrrolidine) | 22 | 25 | 55 |
| $CH_3$ | diisopropyethylamine, 4.2ml | DMSO, 5.3 ml | 69 | 25 | 9 |
| $CH_3$ | N-methylpiperazine, 3.65 ml | (N-Me-piperazine) | 27 | 25 | 14.6 |

EXAMPLE V

A. A solution of 1.0g of methyl 1-methylpyrrole-2-glyoxylate in 2.66 ml pyridine and 10.6 ml of DMSO is cooled to −60° C. and 1.8g hydrogen sulfide is added. The reaction mixture is sealed in a pressure bottle and stirred for 4 hrs. at room temperature. The pressure is then released and the reaction mixture diluted with chloroform and analyzed by gas liquid chromatography. A 23% conversion to methyl 1-methylpyrrole-2-acetate is observed.

B. By the following the procedure of Example V-A, but substituting an equivalent amount of DMF and HMPA for the DMSO solvent, the following respective conversions are found: 5.5% for DMF and 6.0% for HMPA.

EXAMPLE VII

The experimental conditions of Sheithauer and Mayer are employed utilizing ethyl 1-methylpyrrole-2-glyoxylate as the starting material for conversion to ethyl 1-methylpyrrole-2-acetate. Hydrogen sulfide is bubbled vigorously through a stirred solution of 1g of ethyl 1-methylpyrrole-2-glyoxylate, 1 ml of pyridine and 9 ml of DMF for 4 hrs. at 25° C. The mixture is analyzed by gas liquid chromotagraphy. A 1.1% conversion to ethyl 1-methylpyrrole-2-acetate is measured.

EXAMPLE VIII

A solution of methyl 1-methylpyrrole-2-glyoxylate is treated with hydrogen sulfide as in the preceding example. A 2.3% conversion to methyl 1-methylpyrrole-2-acetate is measured.

I claim:

1. In a method of reducing a loweralkyl 1-loweralkyl-pyrrole-2-glyoxylate to a loweralkyl 1-loweralkyl-pyrrole-2-acetate by the amine-catalyzed action of hydrogen sulfide in a tertiary amine solvent or a dipolar aprotic organic solvent, the improvement which comprises said reduction being conducted under a pressure of at least 30 p.s.i. to about 1000 p.s.i.

2. In a method of reducing a loweralkyl 1-loweralkyl-pyrrole-2-glyoxylate to a loweralkyl 1-loweralkyl-pyrrole-2-acetate by the amine-catalyzed action of hydrogen sulfide in a tertiary amine solvent or a dipolar aprotic organic solvent, the improvement which comprises said reduction being conducted under a pressure of from about 50 to about 500 p.s.i.

3. In the method of reducing methyl 1-methyl-pyrrole-2-glyoxylate to methyl 1-methyl-pyrrole-2-acetate by the amine-catalyzed action of hydrogen sulfide in a tertiary amine solvent, the improvement which comprises said reduction being conducted under a pressure of from about 50 to about 500 p.s.i.

4. In the method of reducing methyl 1-methyl-pyrrole2-glyoxylate to methyl 1-methyl-pyrrole-2-acetate by the amine-catalyzed action of hydrogen sulfide in pyridine, the improvement which comprises said reduction being conducted under a pressure of from about 50 to about 500 p.s.i.

* * * * *